| United States Patent [19] | [11] Patent Number: 5,068,436 |
|---|---|
| May | [45] Date of Patent: Nov. 26, 1991 |

[54] HYDROGENATION OF HALONITROBENZENES WITHOUT DEHALOGENATION

[75] Inventor: Donald D. May, Chadds Ford, Pa.

[73] Assignee: E. I. du Pont de Nemours and Company, Wilmington, Del.

[21] Appl. No.: 321,389

[22] Filed: Mar. 10, 1989

[51] Int. Cl.$^5$ .......................................... C07C 209/00
[52] U.S. Cl. ..................................................... 564/417
[58] Field of Search ................................ 564/417, 418

[56] References Cited

U.S. PATENT DOCUMENTS 3,929,891 12/1975 Habig et al. ........................ 564/417
4,020,107 4/1977 Kosak .................................. 564/417

FOREIGN PATENT DOCUMENTS 59-216855 12/1984 Japan .................................. 564/417
1314755 4/1973 United Kingdom ................ 564/417
1440991 6/1976 United Kingdom ................ 564/417

*Primary Examiner*—Richard L. Raymond
*Assistant Examiner*—Scott C. Rand

[57] ABSTRACT

A method for inhibiting dehalogenation of fluorinated and chlorinated benzenoid nitro compounds during catalytic hydrogenation to make the corresponding substituted anilines by conducting the hydrogenation reaction in the presence of an acidic catalytic medium.

8 Claims, No Drawings

HYDROGENATION OF HALONITROBENZENES WITHOUT DEHALOGENATION

BACKGROUND OF THE INVENTION

1. Field of the Invention

This invention relates to the improved process for hydrogenation of chloronitrobenzene and fluoronitrobenzene compounds which have acid functionalities, i.e., substituents, and more particularly, to a method whereby dehalogenation of the halonitrobenzene compound can be eliminated during hydrogenation by conducting the reaction in the presence of an acidic catalytic medium.

2. Description of the Prior Art

Catalytic hydrogenation of halogenated nitrobenzene compounds, and the tendency for such compounds to dehalogenate during the process, have been widely reported. Many patents, for example, describe processes for producing halogenated benzenoid amines by catalyzed hydrogenation of the corresponding halogenated benzenoid nitro compounds. Dehalogenation of the benzenoid nucleus, however, usually occurs concurrently with hydrogenation, i.e., reduction of the nitro group, which in turn, may often result in the formation of undesirable by-products. A variety of additives have been used in conjunction with catalysts in an attempt to inhibit and/or minimize dehalogenation. U.S. Pat. No. 3,929,891 discloses a process whereby dehalogenation is limited to less than 0.2% by sulfitizing the platinum catalyst in an acidic suspension previously saturated with hydrogen. The benzenoid nitro compounds which are hydrogenated by the process do not have acidic substituents and this is an essential characteristic of the compounds used in this process. BE 769-220 discloses the preparation of 3-difluorochloromethyl aniline by Group VIII precious metal or metal oxide catalyzed hydrogenation of 3-nitro-difluorochloromethyl benzene. The reaction is conducted in a water miscible solvent in the presence of at least one mole of HCl. The function of the acid is to increase yield and is not to inhibit dehalogenation. Netherlands Patent Publication No. 7311-193 discloses the hydrogenation of nitrobenzenes having substituent halogen, haloalkyl or aliphatic sulfonyl groups using Raney Nickel as the catalyst. The reaction is conducted in an aqueous buffered medium maintaining the pH between 6-7.5 in order to minimize dehalogenation.

SUMMARY OF THE INVENTION

The present invention is an improvement in a process for the catalyzed hydrogenation of fluorinated and chlorinated benzenoid nitro compounds having acidic substitutents to produce corresponding substituted anilines, the improvement comprising introducing an amount of acid equivalent to the catalyst employed on a molar basis into the hydrogenation mass, said acid having a dissociation constant pKa value of 5 or less. The improvement is, in effect, a method for inhibiting dehalogenation of the benzenoid nitro compounds during catalytic hydrogenation. The preferred acids are selected from the group consisting of concentrated hydrochloric acid, phosphoric acid, hydrobromic acid, and glacial acetic acid.

The presence of a small amount of acid, or mixture of acids, in the hydrogenation mass unexpectedly inhibits dehalogenation of the substrate benzenoid nitro compound during the hydrogenation process so that the desired corresponding substituted aniline can be recovered in high yield and high purity.

DETAILED DESCRIPTION OF THE INVENTION

According to the improved process of the invention, fluorinated or chlorinated benzenoid nitro compounds (I) having acidic functionalities comprising hydroxy, sulfonic or carboxylic substituents are hydrogenated in the presence of an acidized catalyst to obtain the corresponding substituted anilines (A) without defluorination or dechlorination of the halonitrobenzene compound. The product anilines (A) contain less than 0.5%, but usually less than 0.2%, of unwanted components (B) which otherwise could result from dehalogenation of the precursor nitro compound. Yields of the desired halogenated anilines (A) are in excess of 99.5%.

The process improvement of the invention and the precursor nitro compounds (I) to which it applies is illustrated by the following generalized equation:

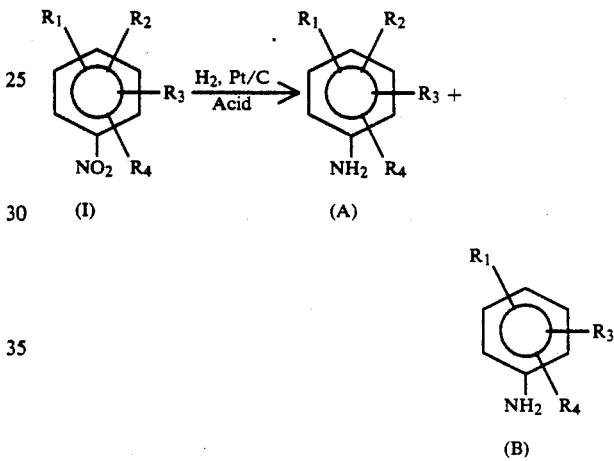

where:
$R_1$ = acidic substituent selected from OH, SO$_3$H, CO$_2$H;
$R_2$ = F or Cl;
$R_3$ = H, F, or Cl; and
$R_4$ = H or CF$_3$.

The molar ratio of A/B is greater than 200.

The process improvement of the invention is especially applicable to the hydrogenation of benzenoid nitro compounds in which $R_1$, the acidic substituent, is hydroxyl; $R_2$ is chlorine; $R_3$ is either hydrogen or chlorine; $R_4$ is hydrogen; and the nitro group occupies the para position with respect to the acidic substituent. Examples of substituted anilines which can be prepared by the hydrogenation of halogenated benzenoid nitro compounds having acidic substituents according to the invention are the following: 2,6-dichloro-4-aminophenol; 2-chloro-4-aminophenol; 2-fluoro-4-aminophenol; 2-chloro-6-difluoromethyl-4-aminophenol; 2-fluoro-6-trifluoromethyl-4-aminophenol; 2-chloro-4-aminobenzoic acid; 2-fluoro-4-aminobenzoic acid; 2-chloro-4-amino-sulfonic acid; 2-fluoro-4-aminosulfonic acid; 2-chloro-6-trifluoromethyl-4-aminobenzoic acid; 2-fluoro-6-trifluoromethyl-4-aminobenzoic acid; 2-fluoro-6-trifluoromethyl-4-aminosulfonic acid; 2,6-dichloro-4-aminobenzoic acid; 2,6-dichloro-4-aminosulfonic acid; 2-chloro-6-fluoro-4-aminophenol; 2-chloro-6-fluoro-4-aminobenzoic acid; 2-chloro-6-fluoro-4-aminosulfonic acid; 2,6-difluoro-4-aminophenol; 2,6- difluoro-4-aminobenzoic acid; 2,6-difluoro-4-aminosulfonic acid; 2,6-difluoro-3-trifluoromethyl-4-aminophenol; 2,6-difluoro-3-trifluoromethyl-4-aminobenzoic acid; 2,6-difluoro-3-trifluoromethyl-4-aminosulfonic acid; 4-chloro-6-aminophenol; 3-chloro-5-aminophenol; 2,4-dichloro-6-aminophenol; 3,6-dichloro-5-aminophenol; 2,4-dichloro-6-aminobenzoic acid; and 3,6-dichloro-5-aminosulfonic acid.

The hydrogenation reaction is conducted in a high pressure autoclave of the type commercially available from Parr Instrument Company. The autoclave is fitted with a double blade pitched agitator which will turn at from 900 to 1000 rpm and a spiral internal cooling coil which runs the full length of the vessel. The reaction vessel is constructed of a corrosion resistant material, such as Hastelloy C and is equipped with a pressure relief device. Heating is provided by an external jacket.

The benzenoid nitro compound is dissolved in a water-miscible organic solvent, such as alcohol, ether or amide. Dimethylformamide (DMF) is a preferred solvent for the reaction. In DMF there is a small amount of impurity produced, however, it is generally less than one percent and does not adversely affect yields obtained in the process.

The hydrogenation catalyst for use in the process is selected from the group consisting of noble metals, such as rhodium, palladium, iridium, and platinum, on an inert supporting matrix, such as charcoal; or Raney nickel or cobalt catalyst compositions can be used. Preferably, the catalyst is an iron modified platinum charcoal catalyst of the type described in U. S. Pat. No. 4,212,824. The catalyst is added to the reaction solution in the autoclave in an amount from about 0.02 to 0.2 weight percent based on the nitro compound being hydrogenated.

The acid upon which the process improvement of the invention is based is used in conjunction with the catalyst and is selected from the group of strong to moderately strong inorganic and organic acids. Acids which are most effective in the process have dissociation constants corresponding to pKa values of 5 or less, and they should be soluble in the solvent which is selected for use. Preferably, the amount of acid employed in the reaction is equivalent to the amount of catalyst being used on a molar basis. Larger or smaller amounts of acid may also be used, however, no particular advantage is observed. The preferred acids are selected from the group consisting of concentrated hydrochloric acid (36%), phosphoric acid, hydrobromic acid, and glacial acetic acid. The acid is added to the solution of benzenoid nitro compound and catalyst in a convenient hydrogenation vessel, e.g., an autoclave. The components are mixed by stirring. Contemplated equivalents for the acids are acidic mixtures comprising two or more of the acids listed above so long as the pKa value for the mixture is 5 or less.

The autoclave and contents are then purged with nitrogen and then hydrogen and finally pressurized with hydrogen. The reaction mass is then brought to the required temperature and pressure while stirring. Temperatures in the range of 50° to 150° C. are suitable; although satisfactory results are achieved at a temperature of, preferably, 90° C. Pressure may be as high as 2000 psig, but 50 to 1000 psig is adequate for most reductions with 450 psig being the preferred pressure.

The following examples serve to illustrate the invention.

EXAMPLE 1

A 1 liter hydrogenation vessel of the type commercially available from Parr Instrument Company was fitted with a double blade pitched agitator which turns at 960 rpm with a spiral internal cooling coil which runs the full length of the vessel. The reaction vessel was constructed of Hastalloy C and was equipped with a pressure relief device. Heating was provided by an external jacket. 120 g of 2,6 dichloro-4-nitrophenol, 400 ml of N,N dimethylformamide, 1 ml of acetic acid and 0.5 g of iron modified platinum on carbon catalyst were placed into the vessel. The contents were purged with nitrogen, hydrogen and finally pressurized to 450 psi with hydrogen. The reaction mass was heated, stirred and quickly reached an operating temperature of 100° C. Hydrogen uptake ceased after one hour, after which the contents were stirred under hydrogen for an additional hour, cooled, filtered and analyzed by Gas Chromatography. The yield of 2,6 dichloro-4-aminophenol (A) was 99.8% with 0.2% monochloro-4-aminophenol (B).

In the absence of acetic acid, the yield of (A) was 99.3% with 0.7% of (B).

COMPARATIVE EXAMPLE

The reaction described in Example 1 was repeated except 1 ml morpholine was added instead of acetic acid. The yield of (A) was 90%, (B) was 1% and unreduced nitro 10%.

EXAMPLE 2

The reaction described in Example 1 was repeated except 1 ml of hydrochloric acid, was added instead of acetic acid. The yield of (A) was 99.9% and (B) was less than 0.1%.

EXAMPLE 3

The reaction described in Example 1 was repeated except 1 ml of phosphoric acid was added instead of acetic acid. The yield of (B) was less than 0.1%.

EXAMPLE 4

The reaction of Example 1 was repeated except 400 ml of n-methyl pyrrolidinone was used as solvent instead of N,N-dimethylformamide. The yield of (B) was less than 0.1%.

EXAMPLE 5

The reaction in Example 1 was repeated except 400 ml of N,N-dimethylacetamide was used instead of N,N-dimethylformamide. The yield of (B) was less than 0.1%.

EXAMPLE 6

120 g of 2,6-dichloro-4-nitrophenol, 400 ml of butanol, 1 ml of acetic acid and 0.5 g iron modified platinum on carbon catalyst were placed into the vessel described in Example 1. The contents were stirred under 450 psi hydrogen for 2 hours at 90° C. The contents were then filtered hot to remove the catalyst, and the filtrate was cooled to 0° C. with stirring to yield purple-black crystals which were collected by filtration. The product analyzed as 99.9% of (A) and 0.1 % of (2). The isolated yield of (A) was 80–90%.

What is claimed is:

1. In a process for the catalyzed hydrogenation of fluorinated and chlorinated benzenoid nitro compounds having acidic substituents to produce the corresponding substituted anilines, the improvement comprising introducing an amount of acid equivalent to the catalyst employed on a molar basis into a hydrogenation mass, said acid having a dissociation constant pKa value of 5 or less.

2. In a process for catalytically hydrogenating fluorinated and chlorinated benzenoid nitro compounds having acidic substituents and defined by the following equation:

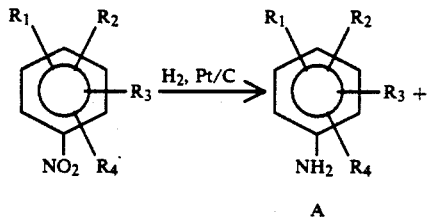

A

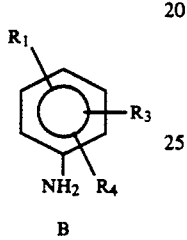

B where:
  $R = OH, SO_3H, CO_2H$;
  $R_2 = F$, or $Cl$;
  $R_3 = H, F$, or $Cl$;
  $R_4 = H$ or $CF_3$; and
the molar ratio of A/B is greater than 200 to produce the corresponding substituted anilines, the improvement comprising introducing an amount of an acid equivalent to the catalyst employed on a molar basis into the hydrogenation mass, said acid having a dissociation constant pKa value of 5 or less.

3. The process of claim 2 wherein
  $R_1 = OH$;
  $R_2 = Cl$;
  $R_3 = H$ or $Cl$;
  $R_4 = H$; and
the nitro group $NO_2$ occupies the para position with respect to the acidic substituent $R_1$.

4. The process of claim 1, claim 2 or claim wherein the acid is selected from the group consisting of concentrated hydrochloric acid, phosphoric acid, hydrobromic acid, and glacial acetic acid.

5. The process of claim 1 wherein the acidic substituents are selected from hydroxy, sulfonic and carboxylic.

6. In a process for catalytically hydrogenating fluorinated and chlorinated benzenoid nitro compounds (I) having an acidic substituent $R_1$ selected from $OH$, $SO_3H$ and $CO_2H$ and defined by the following equation:

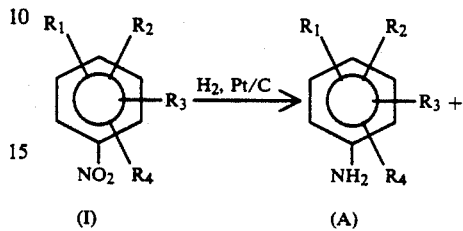

(I)                                            (A)

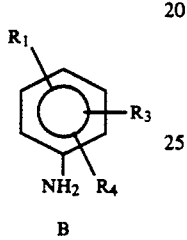

(B)

to produce corresponding substituted anilines, (A), in which the ratio of A/B is greater than 200, a method for inhibiting dehalogenation of said benzenoid nitro compounds during hydrogenation comprising introducing into the hydrogenation mass an amount of an acid selected from the group consisting of concentrated hydrochloric acid, phosphoric acid, hydrobromic acid, and glacial acetic acid equivalent to the catalyst employed on a molar basis into the hydrogenation mass, said acid having a dissociation constant pKa value of 5 or less.

7. In a process for catalytically hydrogenating 2,6-dichloro-4-nitrophenol to produce 2,6-dichloro-4-aminophenol, the improvement comprising introducing an amount of concentrated hydrochloric acid or acetic acid equivalent to the catalyst employed on a molar basis into the hydrogenation mass, said acid having a dissociation constant pKa value of 5 or less.

8. The process of claim 6 in which the nitro group $NO_2$ occupies the para position with respect to the acidic substituent $R_1$.

* * * * *

UNITED STATES PATENT AND TRADEMARK OFFICE
CERTIFICATE OF CORRECTION

PATENT NO. : 5,068,436
DATED : November 26, 1991
INVENTOR(S) : Donald D. May

It is certified that error appears in the above-identified patent and that said Letters Patent is hereby corrected as shown below:

Column 5, line 48, after the words "or claim" insert --3--.

Signed and Sealed this

Twenty-fifth Day of May, 1993

Attest:

MICHAEL K. KIRK

Attesting Officer

Acting Commissioner of Patents and Trademarks